United States Patent [19]
Narayanan et al.

[11] 3,985,885
[45] Oct. 12, 1976

[54] ISOTHIOCYANOBENZOTHIAZOLES

[75] Inventors: Venkatachala Lakshmi Narayanan, Hightstown; Richard G. Angel, Trenton, both of N.J.

[73] Assignee: E. R. Squibb & Sons, Inc., Princeton, N.J.

[22] Filed: Sept. 19, 1975

[21] Appl. No.: 615,027

[52] U.S. Cl. .......................... 424/263; 260/250 BN; 260/256.5 R; 260/304 R; 424/250; 424/251; 424/270
[51] Int. Cl.² .................................. C07D 417/04
[58] Field of Search ............... 260/294.8 C, 304 T; 424/263, 270

[56] References Cited
UNITED STATES PATENTS
3,853,894   12/1974   Haugwitz et al. ............ 260/294.8 C

*Primary Examiner*—Alan L. Rotman
*Attorney, Agent, or Firm*—Lawrence S. Levinson; Merle J. Smith; Burton Rodney

[57] ABSTRACT

Isothiocyanobenzothiazoles are provided having the structure

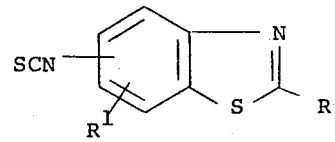

wherein R and R¹ are as indicated below, and which are useful as anthelmintic agents.

14 Claims, No Drawings

ISOTHIOCYANOBENZOTHIAZOLES

BRIEF DESCRIPTION OF THE INVENTION

The present invention relates to isothiocyanobenzothiazoles having the structure

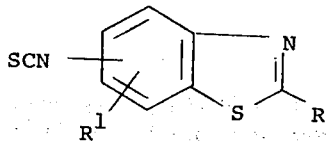

wherein R is a 5- or 6-membered substituted or unsubstituted heterocyclic radical containing one or two hetero atoms, namely, N, O or S; and $R^1$ is hydrogen, halogen, lower alkyl, lower alkoxy, lower alkylthio or arylthio.

The term "halogen" as used throughout the specification refers to fluorine, chlorine, bromine, and iodine; chlorine is preferred.

The 5- or 6-membered heterocyclic radical mentioned above includes heterocyclics such as pyridine, pyrazine, pyrimidine, oxazole, thiophene, pyrrole, furan or thiazole which may be substituted at a carbon atom with a lower alkyl group, halogen, phenylthio or lower alkoxy, or at a secondary nitrogen atom (where present) with a lower alkyl.

The heterocyclic ring is attached at any available carbon atom as for example 2-, 3- or 4-pyridyl; 2- or 3-furyl, etc.

The lower alkyl groups represented by the above groups include straight or branched chain aliphatic hydrocarbon radicals having up to and including seven carbon atoms, such as methyl, ethyl, propyl, isopropyl, butyl, isobutyl, t-butyl, amyl, hexyl, heptyl and the like. The lower alkyl groups can include as substituents any of the aryl groups mentioned below as well as halogen.

The lower alkoxy group includes straight and branched chain radicals of up to and including seven carbon atoms, corresponding to the above alkyl groups, e.g., methoxy, ethoxy, propoxy, isopropoxy and the like.

The "aryl" portion of the arylthio radical includes monocyclic or bicyclic monovalent aromatic ring systems such as phenyl or naphthyl. These aryl radicals can include as substituents halogen, lower alkyl, trifluoromethyl or lower alkoxy.

Preferred are those compounds of formula I wherein NCS is in the 5- or 6- position, $R^1$ is in the 6- or 5-position, that is the position not occupied by the NCS group, and can be hydrogen, lower alkyl, such as methyl, lower alkoxy such as methoxy, halo, such as chloro, or phenylthio, and R is any of the following preferred R heterocyclics:

The isothiocyanobenzothiazoles of formula I are prepared by reacting an aminobenzothiazole of formula II with

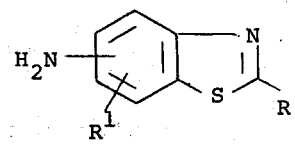

a.

in a relatively non-polar solvent, such as chloroform, ether, tetrahydrofuran, etc., preferably in the presence of an acid acceptor, such as calcium carbonate, triethylamine, etc. at temperatures from 0° to 60° C. More specific reaction procedures are disclosed in Houben-Weyl, 4th Edition, Vol. 9, pages 867 and 88 (1955) and the use of acid binding agents is disclosed in Arch. Pharm. 295, 146–151 (1962).

b. N,N-di(lower alkyl)thiocarbamoyl halide, wherein said halo atom is chlorine or bromine, in an organic solvent, such as benzene, toluene, ethylene dichloride or chlorobenzene at temperatures of from about 40° to about 200° C [J. Org. Chem. 30, 2465 (1965)]

c. a bis-thiocarbamoyl sulfide of the formula

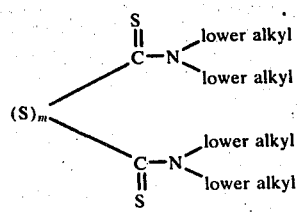

wherein m is one or two and lower alkyl is preferably ethyl in the presence of a hydrogen halide at room

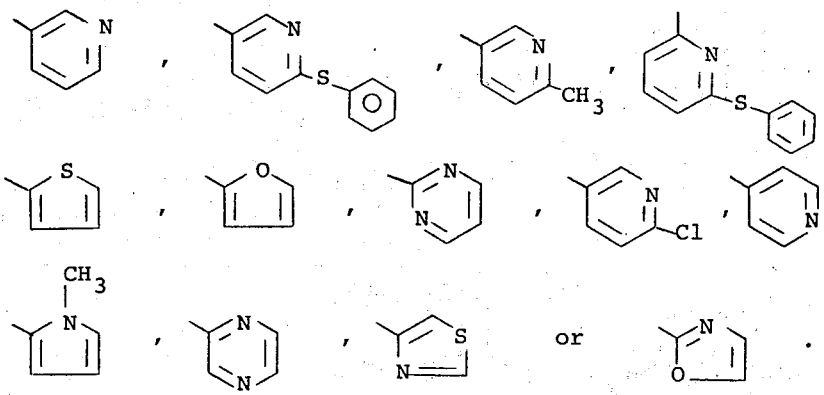

temperature to the refluxing temperature of the organic solvent used, such as chlorobenzene [*Helv. Chim. Acta* 49, 1716 (1966)]
d. bis-trichloromethyl penta-thiodiperoxycarbomate wherein said amine is present in an excess (3:1) [*Angew. Chem.* 78, 985 (1966)].
e. ammonium rhodanide in the presence of gaseous hydrogen chloride in the manner shown in British Pat. No. 1,099,768.
f. phosgene and phosphorus pentasulfide in the general manner described in Houben-Weyl, 4th Edition, Vol. 9, pages 867 and 88 (1955)
g. carbon disulfide in the presence of an inorganic or organic base, such as triethylamine, potassium carbonate, etc. followed by oxidative dehydrosulphurisation with a metal salt (British Pat. No. 793,802) such as lead, copper, zinc or iron (III) salts, iodine, alkali metal hypochlorites or chlorites, preferably the sodium or potassium salts (French Pat. No. 1,311,855), acid halides such as phosgene and phosphorus oxychloride [*Chem Ber.* 98, 2425-2426 (1965)], chlorine and ammonium sulfide (DAS 1,198,189) or chloramine T (British Pat. No. 1,024,913).
h. ammonium rhodanide and benzoyl chloride, followed by thermal decomposition in a refluxing solvent such as chlorobenzene [Houben-Weyl, 4th Edition, 9, 867 and 88 (1955)].
i. carbon disulfide, dicyclohexyl carbodiimide and a tertiary amine such as pyridine or triethylamine at temperatures of from about −10° to about 30° C for from about 0.5 to about 24 hours [*Chem. Ber.* 101, 1746 (1968)].
j. carbon disulfide and butyllithium.

The product from the above reactions may be purified by crystallization from solvents such as benzene, ethylacetate, chloroform, acetonitrile, petroleum ether, benzene-petroleum ether or chromatographed over silica or alumina column. Where the product is obtained in the form of a mixture of isomers, for example 5- and 6-isothiocyanato compounds, such mixtures may be separated by conventional techniques, such as column chromatography.

The required aminobenzothiazoles II are prepared from their corresponding nitro derivatives III by reduction, preferably chemically, by using reagents such as $SnCl_2$, $Fe/CH_3CO_2H$, $Na_2S_2O_4/CH_3OH$, $N_2H_4$ or $NaBH_2S_3$. Analytically pure nitro compounds of structure III may also be reduced catalytically using $PtO_2/H_2$

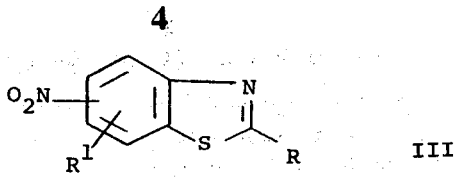

The nitrobenzothiazoles III are made conveniently by nitrating benzothiazoles of formula IV with a mixture of nitric and sulphuric acids.
1. M. T. Bogert & I. Fox, *J.A.C.S.* 52, 2013 (1930)
2. M. T. Bogert & M. Meyer, *J.A.C.S.* 44, 1568 (1922)
3. L. Katz, *J.A.C.S.* 73, 4007 (1951)
4. A. Martvon, J. Suva, and M. Cernayova; *Coll. Czechoslov. Chem. Commun.* 39, 1357 (1974)).

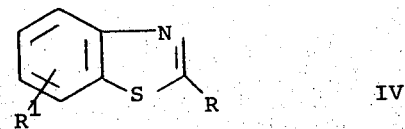

Methods for the synthesis of IV are described in the literature, examples of which are as follows: E. S. Schipper and A. R. Day in "Heterocyclic Compounds", Vol. 5, R. C. Elderfield, Ed; John Wiley and Sons, Inc., New York, N.Y. 1957 p. 506. The preferred method for the synthesis of IV is the reaction of an o-aminothiophenol V with (a) a carboxylic acid or its derivatives VI or (b) an aldehyde VII

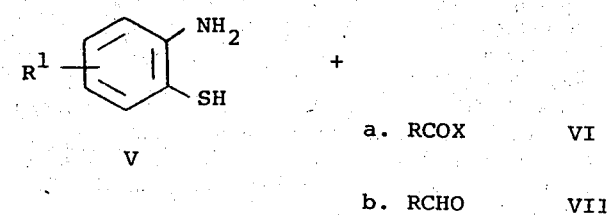

6-Substituted 2-aminobenzothiazoles are prepared by the action of ammonium thiocyanate and bromine on p-substituted anilines according to the reaction:

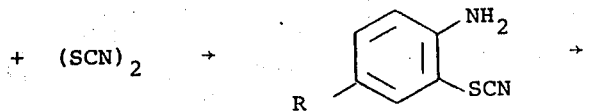

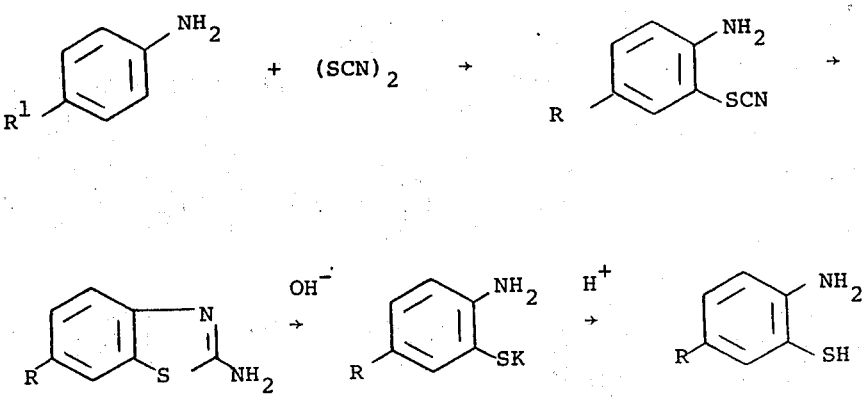

1. R. Adams, *Org. Reactions*, 3, 240 (1957).
2. R. M. Mital and S. K. Jain, *J. Chem. Soc.* (c) 2148, 1969
3. R. L. Dannley & D. A. Zazaris, *Canadian Journal of Chem.* 43, 2610 (1965)).

The compounds of formula I form physiologically acceptable acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Then any other salt may again be formed from the free base and the appropriate inorganic acid. Illustrative are the hydrohalides, especially the hydrochloride and hydrobromide which are preferred, sulfate, nitrate, phosphate, oxalate, tartrate, maleate, fumarate, citrate, succinate, methanesulfonate, benzenesulfonate, toluenesulfonate and the like.

The publications cited for the introduction of the isothiocyanato group are incorporated by reference.

The compounds of formula I have anthelmintic activity and are useful in the treatment and/or prevention of helminthiasis, a parasitic disease which causes widespread and often serious infection in domesticated animals such as swine, horses, cattle, dogs, cats and sheep. The compounds are useful in treating infections caused by haemonchus, ostertagia, trichostrongylus, cooperia, nematodirus, bunostomum, strongylorides, oesophagostomum, trichiuris and moniezia. In treating domesticated animals, the compounds are given orally and may be mixed with a nontoxic, edible carrier to form a feed supplement, or be administered in unit dosage forms such as powders, capsule, tablet, boluses, drenches, etc.

In general, the compounds of formula I exhibit anthelmintic activity when administered to animals in a daily dose of about 10 to about 200 mg per kilogram of animal body weight. It is preferred to employ in the range of 20–100 mg per kilogram of body weight per day. The compounds may be given in a single dose or divided into a plurality of smaller doses. When the compounds are to be employed primarily as prophylactic agents for the prevention of helminthic infections, the preferred daily dose level is, of course, lower than the therapeutic level is, preferably in the range of about 2–20 mg per kilogram of body weight.

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent (5–50%, preferably 10–30%) intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1–2%. Lastly, feeds containing the active ingredient may be made directly by mixing said active ingredient in a feed which is inert to said anthelmintic compounds so as to give feeds having concentrations of anthelmintic agent of from 0.1–2%.

The following examples are provided for illustrative purposes and may include particular features of the invention; however the examples should not be construed as limiting the invention, many variations of which are possible without departing from the spirit or scope thereof. All temperatures are in degrees centigrade.

EXAMPLE 1

5-Isothiocyanato-2-(2-pyridinyl)benzothiazole

A. 2-(2-Pyridinyl)benzothiazole

To a solution of polyphosphoric acid ethyl ester (PPE) 360 g in 600 ml of $CHCl_3$ is added o-aminothiophenol 36.9 g, 0.30 mole and picolinic acid 55.5 g, 0.45 mole. The resulting solution is heated at reflux for 1 hour. The solvent is removed in vacuo, and the residue poured onto 1500 cc of ice-water. The pH of the aqueous mixture is adjusted to 10, and it is then extracted three times with 500 cc portions of $CHCl_3$. The extracts are dried ($MgSO_4$); filtered; and concentrated to dryness. Recrystallization from acetonitrile yields 47.4 g of the title A compound in the form of white needles, m.p. 133°–134°.

B. 5(and 6)-Nitro-2-(2-pyridinyl)benzothiazole 2-(2-Pyridinyl)benzothiazole 46 g, 0.217 mole is dissolved in 200 cc of concentrated $H_2SO_4$, and cooled to 0°. Nitric acid 16 cc, 0.217 mole is added dropwise as the temperature is maintained below 5° C. The temperature is then held at 20° for 2 hours. The resulting solution is poured into 1500 cc of ice water, and the pH adjusted to 8 with 50% NaOH solution. The brown precipitate formed is collected; washed with water; and dried in vacuo. Two recrystallizations from ethanol yield the title B compound in the form of a tan solid m.p. 172°–187°, 16.5 g (30% of theory).

C. 5-(and 6-)Amino-2-(2-pyridinyl)benzothiazole 5-(and 6-)nitro-2-(2-pyridinyl)benzothiazole, 25.6 g (0.1 mole) is dissolved in 100 cc of concentrated HCl and a solution of 78 g of $SnCl_2$ in 100 cc of concentrated HCl is added and the mixture is heated on a steam bath for 1 hour. The mixture is allowed to cool, insolubles are filtered and washed with cold HCl. The product is basified with cold NaOH and the product is filtered and washed with water and dried in vacuo to give 14.8 g of product, m.p. 170°–200°.

D. 5-Isothiocyanato-2-(2-pyridinyl)-benzothiazole

The product from part C is dissolved in tetrahydrofuran, and 7 cc of triethylamine, (0.05 M). Thiophosgene, 2 cc, (0.025 M) is added slowly and the resulting mixture stirred overnight. The insolubles are removed, and washed with tetrahydrofuran. The filtrate is concentrated in vacuo. This crude residue is combined with previously prepared impure samples and placed on a silica gel column. Elution with increasing mixtures of benzene/pentane yield the title compound 1.6 g. The IR and NMR are consistent with the proposed structure (5-isomer).

EXAMPLE 2

6-Isothiocyanato-2-(2-pyridinyl)-benzothiazole 5- and 6-Amino-2-(2-pyridinyl)-benzothiazole 14.8 g, (0.065 M) (prepared as described in Example 1, part C) is dissolved in 400 cc of tetrahydrofuran containing 18.1 cc, 0.13 M, of triethylamine. Thiophosgene 5.0 g, 0.065 M is added, and the mixture stirred at ambient temperature overnight. The precipitate which forms is filtered and washed with tetrahydrofuran. The filtrate is concentrated to dryness, and the residue chromatographed on a silica gel column. Elution with benzene gives the two isomeric isothiocyanates; 5-isothiocyanato-2-(2-pyridinyl)benzothiazole in fractions 9-12, and 6-isothiocyanato-2-(2-pyridinyl)-benzothiazole in fractions 13-18. Recrystallization from acetonitrile give 3.25 g of the former compound, and 9.50 g of the latter (title) compound.

The IR and NMR are consistent with the proposed structures.

EXAMPLE 3

5-Isothiocyanato-2-(3-pyridinyl)benzothiazole

A. 2-(3-Pyridinyl)benzothiazole o-Aminothiophenol 36.9 g (0.30 mole) and nicotinic acid 55.5 g (0.45 mole) are dissolved in 600 cc of chloroform and 360 g of polyphosphoric acid ethyl ester (PPE). The resulting solution is heated at reflux for 1 hour. It is then concentrated to dryness. The residue is poured onto 1500 cc of ice-water, and the resulting mixture is brought to pH 10 with 50% NaOH solution. The aqueous mixture is extracted with $CHCl_3$, and the extracts dried ($MgSO_4$), filtered, and concentrated in vacuo. The residue is recrystallized from acetonitrile to yield the title A compound (42.8 g, 68%, of theory).

B. 5(or 6)-Nitro-2-(3-pyridinyl)benzothiazole 2-(3-Pyridinyl)benzothiazole, 56 g, 0.263 mole (prepared as per part A), is dissolved in 250 cc of cold $H_2SO_4$. Nitric acid, 16.7 cc, 0.263 mole, is added dropwise as the temperature is maintained below −5° C. The reaction mixture is stirred for 2 hours at ambient temperature. It is then poured onto ice, and the pH adjusted to 10 while the temperature is maintained below 20°. The precipitated solid is filtered, and washed with hot water. Drying in vacuo yields 63 g of product, m.p. 220°–230°, 93% of theory.

C. 5-Amino-2-(3-pyridinyl)benzothiazole 1. 5-Nitro-2-(3-pyridinyl)benzothiazole

2-Amino-4-nitrobenzenethiol, 17 g, 0.10 mole, and nicotinic acid, 18.7 g, 0.15 mole, are heated 2 hours at reflux in 250 cc of $CHCl_3$ containing 100 g of PPE. The solution is concentrated in vacuo, and the residue slurried in $H_2O$. The pH is adjusted to 11 with 50% NaOH solution. The precipitate is filtered, washed with $H_2O$ and dried in vacuo to yield 11.2 g of tan solid m.p. 196°–198°, 44% of theory.

2. 5-Amino-2-(3-pyridinyl)benzothiazole

5-Nitro-2-(3-pyridinyl)benzothiazole 11.2 g, 0.044 mole, is dissolved in 45 cc of concentrated HCl. $SnCl_2$, 35 g, in 45 cc of concentrated HCl is added, and the resulting mixture heated for 1 hour on a steam bath. After cooling, the precipitate is filtered, washed in cold HCl and neutralized in cold NaOh solution. The amine is filtered, washed with $H_2O$ and dried to yield 8.0 g of product m.p. 189°–196°.

D. 5-Isothiocyanato-2-(3-pyridinyl)benzothiazole

5-Amino-2-(3-pyridinyl)benzothiazole, 8.0 g, 0.035 M, is dissolved in 400 cc of tetrahydrofuran and 9.8 cc, 0.070 M, of triethylamine. Thiophosgene, 2.7 cc, 0.035 M is added, and the resulting mixture stirred overnight at ambient temperature. The solids which form are filtered and washed with tetrahydrofuran. The filtrate is concentrated to dryness and chromatographed on Alumina IV; elution with benzene yields 1.0 g of white solid which is recrystallized from acetonitrile to yield the title compound, 0.52 g, m.p. 160°–162° (12% of theory).

EXAMPLE 4

5-(and 6-)Isothiocyanato-2-(3-pyridinyl)benzothiazole

A. 5- and 6-Amino-2-(3-pyridinyl)benzothiazole 5- and 6-Nitro-2-(3-pyridinyl)benzothiazole, 42 g, 0.164 mole, is dissolved in 150 ml of concentrated HCl and to that is added a solution of 132 g of $SnCl_2$ in 180 ml of concentrated HCl. The mixture is heated on a steam bath for 1 hour. The precipitate is filtered, and washed with cold HCl. It is then treated with 20% NaOH solution and the solid is washed with water and dried in vacuo to yield 32 g of product, m.p. 189°–194°.

B. 5-(and 6-)-Isothiocyanato-2-(3-pyridinyl)-benzothiazole 5 and 6-Amino-2-(3-pyridinyl)benzothiazole, 32 g, 0.14 M is dissolved in 1 liter of tetrahydrofuran and triethylamine, 39 cc, 0.028 M. Thiophosgene, 10.8 cc, 0.14 M, is added, and the resulting mixture stirred overnight at ambient temperature. The solids which form are filtered and washed with tetrahydrofuran. The filtrate is concentrated to dryness, and chromatographed on silica gel to yield the title, 3.3 g, m.p. 160°–162° (10% yield).

EXAMPLE 5

5-Isothiocyanato-6-methoxy-2-(3-pyridinyl)benzothiazole

A. 6-Methoxy-2-(2-pyridinyl)benzothiazole

A mixture of 2-amino-5-methoxy-benzenethiol, 25 g (0.16 mole) and nicotinic acid, 24.6 g (0.2 mole) is dissolved in 250 cc of $CHCl_3$ containing 160 g of PPE. The mixture is refluxed overnight. The mixture is concentrated to dryness and the residue poured on ice and the pH of the solution is adjusted to 10 using 50% NaOH solution. The precipitate is filtered, washed with water and dried to yield 34.5 g of the title compound.

B. 5-Nitro-6-methoxy-2-(2-pyridinyl)benzothiazole

6-Methoxy -2-(pyridinyl)benzothiazole, 30 g, (0.124 mole) is dissolved in 115 cc of concentrated $H_2SO_4$ and cooled to 0°. Nitric acid, 7.9 cc (0.124 mole) is added and the solution stirred for 2 hours at room temperature. The reaction mixture is poured on ice and the pH adjusted to 10 with 50% NaOH solution. The precipitate is filtered and dried to yield 11 g of product.

C. 5-Amino-6-methoxy-2-(2-pyridinyl)benzothiazole

6-Methoxy-5-nitro-2-(2-pyridinyl)benzothiazole, 11 g (.038 mole) is reduced according to procedure of Example 4A to give 8.5 g of product.

D. 5-Isothiocyanato-6-methoxy-2-(3-pyridinyl)benzothiazole

5-Amino-6-methoxy-2-(2-pyridinyl)benzothiazole, 8.3 g, 0.0325 mole, is dissolved in 400 cc of tetrahydrofuran containing 9.5 cc, 0.065 mole of triethylamine. Thiophosgene, 2.5 cc, 0.0325 mole, is added, and the resulting mixture stirred at ambient temperature for 4 hours. The precipitate which forms is filtered and washed with tetrahydrofuran. The filtrate is concentrated to dryness. The residue is adsorbed on a silica gel column and eluted with hexane-ethylacetate to yield 1.8 g of crude product. Recrystallization from MeCN/CHCl₃ yields 1.2 g of the title product, m.p. 164°–166°.

EXAMPLE 6

5-Isothiocyanato-2-(2-thienyl)benzothiazole

A. 5-Nitro-2-(2-thienyl)benzothiazole

2-Amino-4-nitrobenzenethiol, 9.6 g (0.054 mole) and thiophene-2-carboxylic acid, 10.0 g (0.075 mole) are added to a solution of 54 g of PPE in 130 cc CHCl₃. The mixture is heated at reflux for 2 hours. It is then concentrated in vacuo and the residue poured over ice. The pH is adjusted to 10 with 50% NaOH solution, and the precipitate filtered and washed with H₂O. Drying in vacuo yields 15 g of the title compound.

B. 5-Amino-2-(2-thienyl)benzothiazole

5-Nitro-2-(2-thienyl)benzothiazole, 17 g (0.068 mole) is treated as in Example 4A to yield 7.0 g of product.

C. 5-Isothiocyanato-2-(2-thienyl)benzothiazole

5-Amino-2-(2-thienyl)benzothiazole 7.0 g, 0.03 M is dissolved in 400 cc of tetrahydrofuran and 8.4 cc, 0.06 M, of triethylamine. Thiophosgene 2.3 cc, 0.03 M, is added, and the resulting mixture stirred at ambient temperature overnight. The solids which form are filtered, and washed with tetrahydrofuran. The filtrate is concentrated to dryness, and chromatographed on Alumina IV. The product is recrystallized from acetonitrile to yield 5.7 g of colorless needles, 70% of theory, m.p. 147°–149°.

EXAMPLE 7

5-Isothiocyanato-2-(6-methyl-2-pyridinyl)benzothiazole

Following the procedure of Example 1, but substituting 6-methylpicolinic acid for the picolinic acid, the title compound is obtained.

EXAMPLE 8

5-Isothiocyanato-2-(6-chloro-2-pyridinyl)benzothiazole

Following the procedure of Example 1, but substituting 6-chloropicolinic acid for the picolinic acid, the title compound is obtained.

EXAMPLE 9

5-Isothiocyanato-2-(6-phenylthio-2-pyridinyl)benzothiazole

Following the procedure of Example 1, but substituting 6-phenylthiopicolinic acid for the picolinic acic, the title compound is obtained.

EXAMPLE 10

5-Isothiocyanato-2-(2-furyl)benzothiazole

Following the procedure of Example 1 but substituting 2-furoic acid for the picolinic acid, the title compound is obtained.

EXAMPLE 11

5-Isothiocyanato-2-(2-pyrimidinyl)benzothiazole

Following the procedure of Example 1 but substituting 2-pyrimidine carboxylic acid for the picolinic acid, the title compound is obtained.

EXAMPLE 12

5-Isothiocyanato-2-(2-pyrazinyl)benzothiazole

Following the procedure of Example 1, but substituting 2-pyrazine carboxylic acid for the picolinic acid, the title compound is obtained.

EXAMPLE 13

5-Isothiocyanato-2-(2-oxazolyl)benzothiazole

Following the procedure of Example 1, but substituting 2-oxazoline carboxylic acid for the picolinic acid, the title compound is obtained.

EXAMPLE 14

5-Isothiocyanato-2-(2-thiazolyl)benzothiazole

Following the procedure of Example 1, but substituting 2-thiazole carboxylic acid for the picolinic acid, the title compound is obtained.

EXAMPLE 15

5-Isothiocyanato-6-methyl-2-(3-pyridinyl)benzothiazole

Following the procedure of Example 5, but substituting 2-amino-5-methylbenzenethiol for 2-amino-5-methoxybenzenethiol, the title compound is obtained.

EXAMPLE 16

5-Isothiocyanato-6-phenylthio-2-(3-pyridinyl)benzothiazole

Following the procedure of Example 5, but substituting 2-amino-5-phenylthiobenzenethiol for 2-amino-5-methoxybenzenethiol, the title compound is obtained.

EXAMPLE 17

5-Ethylthio-6-isothiocyanato-2-(3-pyridinyl)benzothiazole

Following the procedure of Example 2 but substituting 4-ethylthio-2-aminobenzenethiol for o-aminobenzenethiol, the title compound is obtained.

EXAMPLE 18

6-Isothiocyanato-2-(4-pyridinyl)benzothiazole

Following the procedure of Example 2, but substituting 4-pyridine carboxylic acid for picolinic acid, the title compound is obtained.

EXAMPLES 19 to 25

Following the procedure of Example 1 but substituting for the o-aminothiophenol, the compound listed in column A of Table I below, and substituting for the picolinic acid, the compound listed in column B, the compound set out in column C is obtained.

TABLE I

| | Column A | Column B | | Column C | | |
|---|---|---|---|---|---|---|
| Ex. No. | R¹ (position) | R | SCN (position) | R¹ (position) | R | |
| 19. | $C_2H_5$ (5) | (pyrazinyl) | 5 | $C_2H_5$ (6) | (as per column B) | |
| 20. | $C_2H_5O$ (4) | (pyrimidinyl) | 6 | $C_2H_5O$ (5) | | |
| 21. | $CH_3S$ (5) | (thienyl) | 5 | $CH_3S$ (6) | | |
| 22. | $C_6H_5S$ (4) | (furyl) | 6 | $C_6H_5S$ (5) | | |
| 23. | Br (5) | (pyrrolyl) | 5 | Br (6) | | |
| 24. | Cl (5) | (dimethylfuryl) | 5 | Cl (6) | | |
| 25. | $C_3H_7O$ (4) | (diethylpyridinyl) | 6 | $C_3H_7O$ (5) | | |

What is claimed is:

1. A compound having the formula

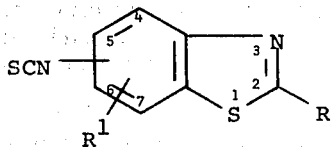

wherein SCN occupies the 5- or 6-position, R is pyridyl or thienyl or such heterocyclic radicals substituted with lower alkyl, halogen, phenylthio or lower alkoxy, and R¹ is a member selected from the group consisting of hydrogen, lower alkyl, lower alkoxy, alkylthio, containing 1 to 7 carbons, naphthylthio, phenylthio, or halogen, R¹ occupying the 5- or 6-position and physiologically acceptable acid-addition salts thereof.

2. A compound as defined in claim 1 wherein R¹ is hydrogen.

3. A compound as defined in claim 1 wherein R¹ is hydrogen or lower alkoxy.

4. A compound as defined in claim 1 wherein R¹ is halo, alkylthio containing 1 to 7 carbons, phenylthio, or naphthylthio.

5. A compound as defined in claim 1 wherein R is pyridine.

6. A compound as defined in claim 1 wherein R is thienyl.

7. A compound as defined in claim 1 having the name 5(and/or 6)-isothiocyanato-2-(3-pyridinyl)benzothiazole.

8. A compound as defined in claim 1 having the name 5-isothiocyanato-2-(3-pyridinyl)benzothiazole.

9. A compound as defined in claim 1 having the name 6-isothiocyanato-2-(2-pyridinyl)benzothiazole.

10. A compound as defined in claim 1 having the name 5-isothiocyanato-2-(2-pyridinyl)benzothiazole.

11. A compound as defined in claim 1 having the name 5-isothiocyanato-6-methoxy-2-(3-pyridinyl)benzothiazole.

12. A compound as defined in claim 1 having the name 5-isothiocyanato-2-(2-thienyl)benzothiazole.

13. A pharmaceutical composition for treating helminthiasis comprising an effective amount of a compound as defined in claim 1 and an inert pharmaceutically acceptable carrier therefor.

14. A method for treating helminthiasis which comprises orally administering to a domesticated animal host an effective amount of the composition as defined in claim 13.

* * * * *

UNITED STATES PATENT AND TRADEMARK OFFICE
CERTIFICATE OF CORRECTION

PATENT NO. : 3,985,885
DATED : October 12, 1976
INVENTOR(S) : Venkatachala Lakshmi Narayanan et al.

It is certified that error appears in the above-identified patent and that said Letters Patent are hereby corrected as shown below:

Column 2, line 2, "formula I" should read --formula II--.
Column 7, line 47, "$H_2So_4$" should read --$H_2SO_4$--.
Column 8, line 4, "NaOh" should read --NaOH--.
Column 8, line 61, after "6-Methoxy -2-(" insert -- 2- --.
Column 9, line 67, "acic" should read --acid--.

Signed and Sealed this

Eighth Day of February 1977

[SEAL]

Attest:

RUTH C. MASON
Attesting Officer

C. MARSHALL DANN
Commissioner of Patents and Trademarks